(12) United States Patent
Shin et al.

(10) Patent No.: US 11,707,566 B2
(45) Date of Patent: *Jul. 25, 2023

(54) PUMP FOR MEASURING PRESSURE OF FLUID TO BE TRANSFERRED, FLUID TRANSPORT SYSTEM USING THE SAME, AND METHOD FOR OPERATING THE SYSTEM

(71) Applicant: SOGANG UNIVERSITY RESEARCH & BUSINESS DEVELOPMENT FOUNDATION, Seoul (KR)

(72) Inventors: Woonsup Shin, Seoul (KR); Enhua Zhu, Seoul (KR); Se Mi Son, Seoul (KR); Young Joo Lee, Seoul (KR)

(73) Assignee: SOGANG UNIVERSITY RESEARCH & BUSINESS DEVELOPMENT FOUNDATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 17/711,318

(22) Filed: Apr. 1, 2022

(65) Prior Publication Data
US 2022/0226565 A1 Jul. 21, 2022

Related U.S. Application Data

(63) Continuation of application No. 16/822,498, filed on Mar. 18, 2020, now Pat. No. 11,318,246, which is a (Continued)

(30) Foreign Application Priority Data

Sep. 19, 2017 (KR) .......................... 10-2017-0120527

(51) Int. Cl.
A61M 5/142 (2006.01)
A61M 5/168 (2006.01)
(Continued)

(52) U.S. Cl.
CPC .... *A61M 5/14224* (2013.01); *A61M 5/16881* (2013.01); *A61M 5/16886* (2013.01);
(Continued)

(58) Field of Classification Search
CPC ................................................. A61M 5/14224
See application file for complete search history.

(56) References Cited

U.S. PATENT DOCUMENTS

| 6,709,383 B2 | 3/2004 | Tsukahara |
| 8,062,007 B2 | 11/2011 | Ikushima |

(Continued)

FOREIGN PATENT DOCUMENTS

| JP | 2006346440 | 12/2006 |
| JP | 2015522929 | 8/2015 |

(Continued)

OTHER PUBLICATIONS

International Search Report of PCT/KR2018/010976 dated Dec. 20, 2018, 2 pages.

*Primary Examiner* — David Z Huang
*Assistant Examiner* — Jean F Morello
(74) *Attorney, Agent, or Firm* — Riverside Law LLP

(57) ABSTRACT

The present invention discloses a pump for measuring a pressure of fluid to be transferred, a fluid transport system using the same, and a method for operating the system. The pump includes a pumping portion alternately generating a positive pressure and a negative pressure; a first diaphragm which is provided on one side of the pumping portion and of which a shape is changed as the positive pressure and the negative pressure are alternately generated; a transport (Continued)

chamber which sucks and discharges a transport target fluid corresponding to the deformation of the first diaphragm; a second diaphragm which is provided on the other side of the pumping portion; a monitoring chamber which is provided on one side of the second diaphragm and of which a pressure changes corresponding to the deformation of the second diaphragm; and a pressure measuring portion measuring a pressure change of the monitoring chamber.

25 Claims, 12 Drawing Sheets

Related U.S. Application Data continuation of application No. PCT/KR2018/010976, filed on Sep. 18, 2018.

(51) Int. Cl.
| | | |
|---|---|---|
| *F04B 43/02* | (2006.01) | |
| *F04B 51/00* | (2006.01) | |
| *F04B 53/10* | (2006.01) | |
| *G01L 9/00* | (2006.01) | |
| *F04B 43/06* | (2006.01) | |
| *G01M 13/00* | (2019.01) | |

(52) U.S. Cl.
CPC .............. *F04B 43/02* (2013.01); *F04B 43/06* (2013.01); *F04B 51/00* (2013.01); *F04B 53/10* (2013.01); *G01L 9/0051* (2013.01); *G01L 9/0072* (2013.01); *G01M 13/00* (2013.01); *A61M 2205/3317* (2013.01); *A61M 2205/3331* (2013.01)

(56) References Cited

U.S. PATENT DOCUMENTS

| | | |
|---|---|---|
| 9,745,971 B2 | 8/2017 | Shin |
| 2004/0018100 A1 | 1/2004 | Takagi |
| 2013/0121880 A1 | 5/2013 | Yamazaki |
| 2016/0169759 A1 | 6/2016 | Kishida |

FOREIGN PATENT DOCUMENTS

| | | |
|---|---|---|
| JP | 2017522929 | 8/2017 |
| KR | 101457629 | 11/2014 |
| KR | 20170013322 | 2/2017 |
| KR | 20170065567 | 6/2017 |

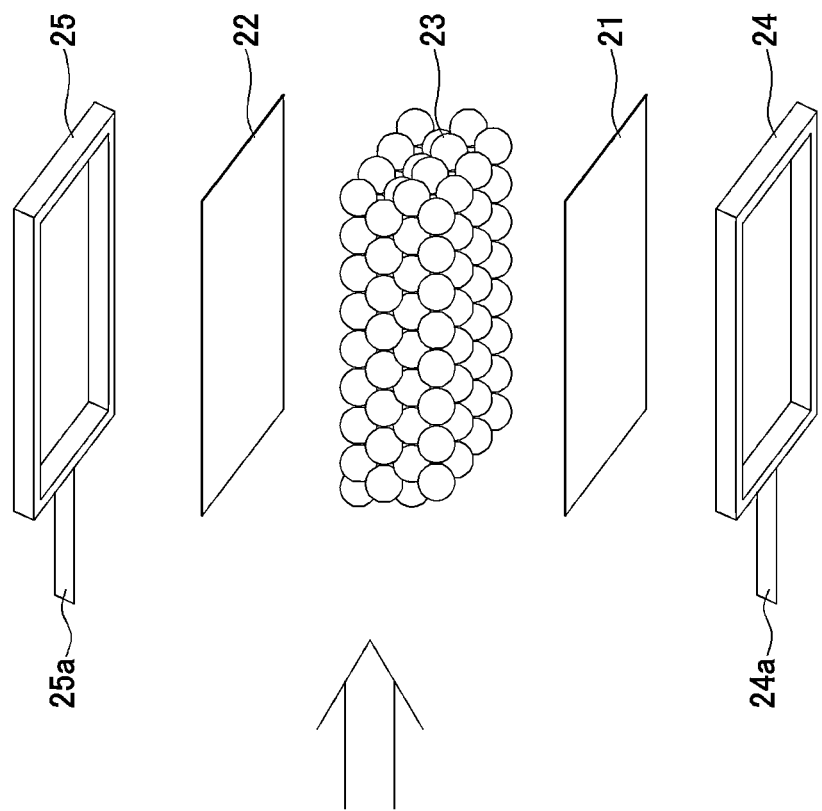
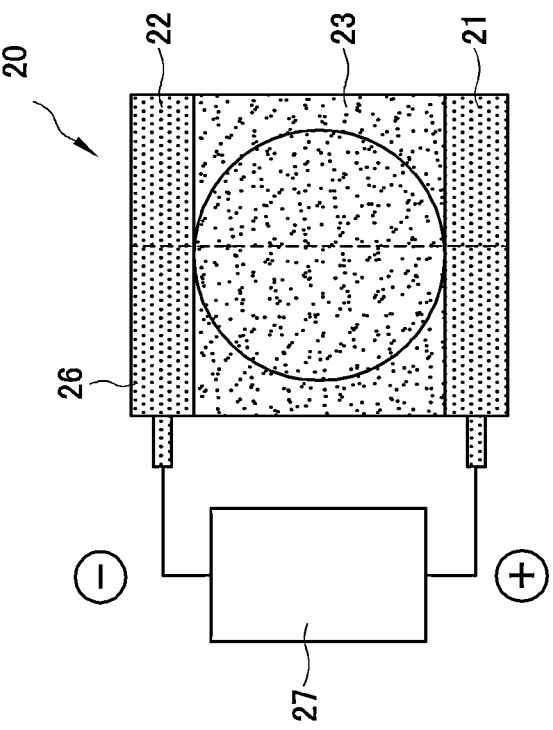

FIG. 2B(ii)

PUMP FOR MEASURING PRESSURE OF FLUID TO BE TRANSFERRED, FLUID TRANSPORT SYSTEM USING THE SAME, AND METHOD FOR OPERATING THE SYSTEM

CROSS-REFERENCE TO RELATED APPLICATION

This application is a continuation of U.S. application Ser. No. 16/822,498 filed Mar. 18, 2020 which claims priority to and the benefit of PCT Patent Application No. PCT/KR2018/010976 filed on Sep. 18, 2018, and Korean Patent Application No. 10-2017-0120527 filed in the Korean Intellectual Property Office on Sep. 19, 2017, the entire contents of which are incorporated herein by reference.

BACKGROUND OF THE INVENTION

1. Field of the Invention

The present invention relates to a pump for measuring a pressure of fluid to be transferred, a fluid transport system using the same, and a method for operating the system.

2. Description of the Related Art

A fixed volume pump is a pump that constantly transports a liquid per unit time. The Pump can be divided into a diaphragm pump (membrane pump), a gear pump, a peristaltic pump, a syringe pump, and the like according to its principle of operation, and is used in a wide range of industries.

In particular, the diaphragm pump pulsates a separating plate of an elastic thin film to perform suction or discharge of a liquid by a volume change, and the diaphragm pump is used for a small capacity pump or a fixed volume pump for drug injection or the like. In the reciprocating pump, a flow of the liquid is intermittent by nature because the suction and discharge of the liquid are repeatedly performed. As a result, inertia is generated in the liquid flowing in a flow path, vibration is continuously generated in the flow path, and thereby the pump may malfunction due to blockage of the flow path or gas generation. In addition, fine foreign matters can also block the flow path, thereby causing the pump to malfunction. Such unstable drive causes difficulties especially in using the diaphragm pump for injecting drugs into the human body.

In an example, an intrathecal drug administration system (ITDAS) is widely used as an intra-body implantable drug infusion pump. The intrathecal drug administration system is mainly used for treatment of cancer pain or chronic pain with severe pain, and is also utilized for a patient with cerebral palsy and spasticity symptoms. In such an intra-body implantable drug infusion pump, an extent to which the catheter blockage or pump malfunction is related to the patient's life is very important. Therefore, a method of embedding a pressure sensor in the flow path for monitoring the pump malfunction has been developed. However, embedding the sensor in the flow path may contaminate the transport target fluid in the flow path, and thus it is difficult for the sensor to be applied to the intra-body implantable drug infusion pump.

In this regard, U.S. Patent Application Publication No. 2013-0121880 (Title of the Invention: AUTOMATIC ANALYZER) discloses contents in which vibration of a specific frequency is given through a pressure transmission medium (vibrator) in a flow path, and then a pressure sensor provided outside the flow path measures an amplitude or a phase of a specific frequency to detect whether or not the liquid is normally sucked into a nozzle. However, because the vibrator or the like has to be further provided, there is still a limitation in that a size of the pump is increased, and when a sample is injected into the human body, the human body may be harmed by the vibration in the flow path.

SUMMARY OF THE INVENTION

The present invention is to solve the problems described above of the related art, and an object of the present invention is to provide a pump formed to efficiently measure a pressure of a flow path without contaminating a liquid in the flow path, a fluid transport system using the same, and a method of operating the system. However, the technical problem to be solved by the present example is not limited to the technical problem as described above, and other technical problems may exist.

As technical means for solving the technical problem described above, a first aspect of the present invention is a pump including: a pumping portion alternately generating a positive pressure and a negative pressure; a first diaphragm which is provided on one side of the pumping portion and of which a shape is changed as the positive pressure and the negative pressure are alternately generated; a transport chamber which is provided on one side of the first diaphragm, and sucks and discharges a transport target fluid corresponding to the deformation of the first diaphragm; a second diaphragm which is provided on the other side of the pumping portion and of which a shape is changed as the positive pressure and the negative pressure are alternately generated; a monitoring chamber which is provided on one side of the second diaphragm and of which a pressure changes corresponding to the deformation of the second diaphragm; and a pressure measuring portion measuring a pressure change of the monitoring chamber.

In addition, a second aspect of the present invention is a fluid transport system including: a pump including a first diaphragm and a second diaphragm which are provided on both sides of a pumping portion alternately generating a positive pressure and a negative pressure, and of which shapes are changed according to the positive pressure and the negative pressure, a transport chamber which sucks and discharges a transport target fluid according to the shape change of the first diaphragm, a monitoring chamber of which a pressure changes according to the shape change of the second diaphragm, and a pressure measuring portion measuring a pressure of the monitoring chamber; a reservoir in which the transport target fluid is stored; a suction path that is a fluid transport path through which the transport target fluid discharged from the reservoir is sucked to the pump; a discharge path that is a fluid transport path of the transport target fluid discharged from the pump; and a control circuit detecting abnormality of the pump by monitoring a pressure value measured by the pressure measuring portion.

In addition, a third aspect of the present invention is a method of operating a fluid transport system using the pump of the first aspect, the method including: (a) a step of alternately supplying voltages of different polarities to a pumping portion such that at least a part of a first diaphragm moves forward and backward, and thereby a transport target fluid is sucked and discharged into a transport chamber provided on one side of the first diaphragm; (b) a step of monitoring a pressure change of a monitoring chamber provided on one side of a second diaphragm; and (c) a step of detecting abnormality of the pump based on a change pattern of pressure values measured for a predetermined time and an average value of the pressure values measured for the predetermined time. In this case, at least a part of the second diaphragm moves forward and backward in a same direction as the first diaphragm as voltages of different polarities are alternately supplied to the pumping portion.

A fourth aspect of the present invention is a computer-readable recording medium on which a program for implementing the method of the third aspect is recorded.

According to the problem solving means of the present invention described above, an air layer through which the same pressure as the pressure transmitted to the transport target body is transmitted to the pump is formed, and a pressure sensor is disposed in the air layer to efficiently measure the pressure value transmitted to the transport target fluid. Furthermore, in the fluid transport system using the pump, it is possible to effectively detect whether or not the pump operates and the flow path is blocked by monitoring the change shape of the pressure value.

BRIEF DESCRIPTION OF THE DRAWINGS

FIG. 2A(i) is a view illustrating a configuration of a pumping portion according to an example of the present invention, and FIG. 2A(ii) is an exploded view illustrating the pumping portion.

DETAILED DESCRIPTION OF THE EMBODIMENTS

Figure 1:
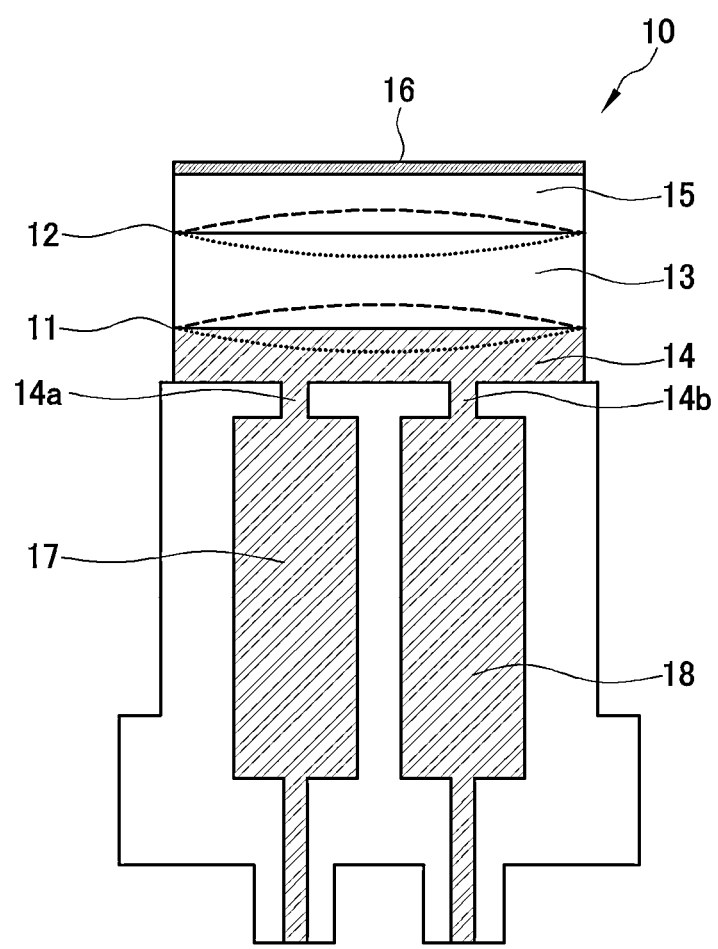
FIG. 1 is a view illustrating a configuration of a pump according to an example of the present invention.

Hereinafter, examples of the present invention will be described in detail with reference to the accompanying drawings so that those skilled in the art may easily implement the present invention. However, the present invention may be embodied in many different forms and is not limited to the examples demonstrated here. In the drawings, portions irrelevant to the description are omitted in order to clearly describe the present invention, and like reference numerals designate like portions throughout the specification.

In the present specification, when a portion is "connected" to another portion, it includes not only "directly connected", but also "electrically connected" with another element interposed therebetween.

Throughout the present specification, when a member is located "on" another member, this includes not only a case in which one member is in contact with another member but also a case in which further another member exists between the two members.

In the present specification, when a portion "includes" a certain configuration element, it means that it further includes other configuration elements, without excluding the other configuration elements unless otherwise stated. The terms "about", "substantially", and the like as used throughout the present specification of the present invention are used at, or in proximity to, the numerical values when manufacturing and material tolerances inherent in the meanings mentioned are given, and in order to prevent unscrupulous infringers from unfair use, accurate or absolute figures are used to aid the understanding of the present invention. As used throughout the present specification of the present invention, a term "step" or "step of" does not mean "step for".

FIG. 1 is a view illustrating a configuration of a pump according to an example of the present invention.

Referring to FIG. 1, a pump 10 according to an example of the present invention includes a pumping portion 13 alternately generating a positive pressure and a negative pressure; a first diaphragm 11 which is provided on one side of the pumping portion 13 and of which a shape is changed according to the positive pressure and the negative pressure; a transport chamber 14 which sucks and discharges a transport target fluid corresponding to the shape change of the first diaphragm 11; a second diaphragm 12 which is provided on the other side of the pumping portion 13 and of which a shape is changed according to the positive pressure and the negative pressure; a monitoring chamber 15 of which a pressure changes corresponding to the shape change of the second diaphragm 12; and a pressure measuring portion 16 measuring a pressure change of the monitoring chamber 15. The monitoring chamber 15 may be filled with gas or a fluid, and the pressure measuring portion 16 may be a pressure sensor that measures a pressure of the gas or the fluid.

First, the pumping portion 13 may include one or more configuration elements that alternately generate the positive pressure and the negative pressure. For example, the pumping portion 13 may include at least one configuration element that alternately transports the negative pressure and the positive pressure with the first and second diaphragms 11 and 12 by causing the fluid and/or gas with which the pumping portion 13 is filled to reciprocate by transforming a rotational force of a motor (not illustrated) into a reciprocating motion.

Alternatively, the pumping portion 13 may include at least one configuration element that causes the fluid and/or the gas to reciprocate through an electrochemical reaction but is not limited thereto. For example, the pumping portion 13 may be implemented using an electroosmotic principle. In this case, the pump 10 is an electroosmotic pump which is operated on a principle that the fluid moves by the electroosmotic phenomenon generated when a voltage is applied by using electrodes at both ends of a capillary tube or a porous membrane. Unlike a mechanical pump, the electroosmotic pump has advantages that there is no mechanical moving portion thereby being silent and effectively controlling a flow rate in proportion to the applied voltage.

FIG. 2A(i) is a view illustrating a configuration of the pumping portion according to an example of the present invention, and FIG. 2A(ii) an exploded view illustrating the pumping portion.

As illustrated in FIGS. 2A(i) and 2A(ii), the pumping portion 13 according to an example of the present invention includes a membrane 23; a first electrode 21 and a second electrode 22 provided on both sides of the membrane 23, respectively; and strips 24 and 25 in which the first and second electrodes 21 and 22 are stored, and which transmit electric power to the first and second electrodes 21 and 22. The strips 24 and 25 have respective connecting members 24a and 25a connected to the power supply portion 27 to transmit the electric power supplied from the power supply portion 27 provided outside the pump 10, to the first and second electrodes 21 and 22.

The pumping portion 13 generates a positive pressure and a negative pressure through a flow of the fluid between the membrane 23, and the first and second electrodes 21 and 22.

Specifically, as illustrated in FIG. 2A(i), the membrane 23 is installed in the fluid path portion 26 through which the fluid moves, and as illustrated in FIG. 2A(ii), the membrane 23 is formed of a porous material or structure to allow the movement of the fluid. The first electrode 21 and the second electrode 22 are provided on both sides of the membrane 23 on the fluid path portion 26, and the first electrode 21 and the second electrode 22 may include a conductive polymer in which an anionic polymer is mixed. Like the membrane 23, the first electrode 21 and the second electrode 22 are formed of a porous material or structure to allow the movement of the fluid.

When a voltage is supplied to first and second electrodes 21 and 22, a voltage difference between the first electrode 21 and the second electrode 22 causes a redox reaction to occur in the first electrode 21 and the second electrode 22, and thereby a charge balance is broken. At this time, charges are balanced by moving cations in the first and second electrodes 21 and 22. In this case, any one of the first electrode 21 and the second electrode 22 may generate cations through an electrochemical reaction, and the other may consume the cations. Here, the cations generated and consumed during the electrochemical reaction may be monovalent cations, but are not limited thereto, and may include various ions such as hydrogen ions (H+), sodium ions (Na+), potassium ions (K+), and the like.

When the ions move according to the redox reaction through the membrane 23, the fluid may move along the fluid path portion 26. In this case, the membrane 23 may allow the movement of ions as well as the fluid. Therefore, when the electric power is supplied to the first and second electrodes 21 and 22, the fluid and ions may be moved from one side to the other side of the membrane 23 or from the other side to one side thereof.

In addition, a conductive polymer may be electrodeposited on the first electrode 21 and the second electrode 22. In the pumping portion 13, the conductive polymer includes a macromolecule polymer, that is, an anionic polymer. In the redox reaction of the first and second electrodes 21 and 22, since the anionic polymer is fixed and cannot be moved, the cations in the fluid move and balance the charge. That is, when the conductive polymer matrix is neutral during the reduction reaction of the negative electrode, the cations present in the fluid are introduced to balance the charge of the fixed anionic polymer. In other words, during the redox reaction of the first and second electrodes 21 and 22, the anion polymer does not move, but the cations in the fluid move. The cations can easily pass through the membrane 23 by action of an attraction force with the negatively charged membrane 23, thereby causing a rapid redox reaction. This means that the pump 10 can move the fluid at high speed.

In this case, the conductive polymer may be formed through polymerization of monomers in the fluid including the anionic polymer. Alternatively, the conductive polymer may be synthesized through electrochemical oxidation or chemical oxidation using an oxidizing agent. In addition, the conductive polymer may be various polymers having electrical conductivity or negative charge.

In addition, the first and second electrodes 21 and 22 may further include a carbon nanostructure such as carbon nanotube (CNT), graphene, and carbon nanoparticle. In the electrode electrodeposited a composite of the conductive polymer including the carbon nanotube in the carbon nanostructure, the redox reaction may occur at a more stable and at a high speed. In addition, the first and second electrodes 21 and 22 may further include metal oxides such as manganese oxide (MnOx), cobalt oxide (CoOx), nickel oxide (NiOx), ruthenium oxide (RuOx), and composites thereof. The first and second electrodes 21 and 22 formed of the metal oxides can be induced movement of cations through a redox reaction.

Meanwhile, the conductive polymer included in the first electrode 21 and the second electrode 22 may cause a reversible electrochemical reaction. That is, the first electrode 21 and the second electrode 22 may have both forward reaction and reverse reaction, respectively. The reversible electrode reaction may be performed by alternately supplying polarities of voltages to the first electrode 21 and the second electrode 22, respectively by the power supply portion 27.

Figure 2B:
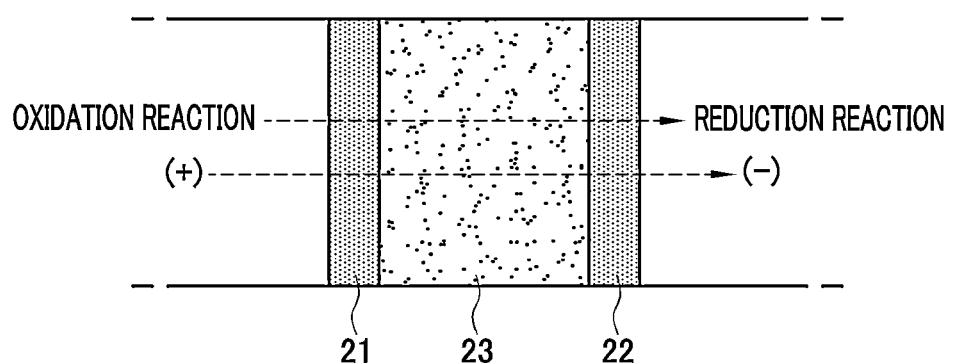
FIGS. 2B(i) and 2B(ii) are views illustrating an example in which a flow of a fluid in the pumping portion changes according to a reversible electrochemical reaction according to an example of the present invention.
Figure 2B:
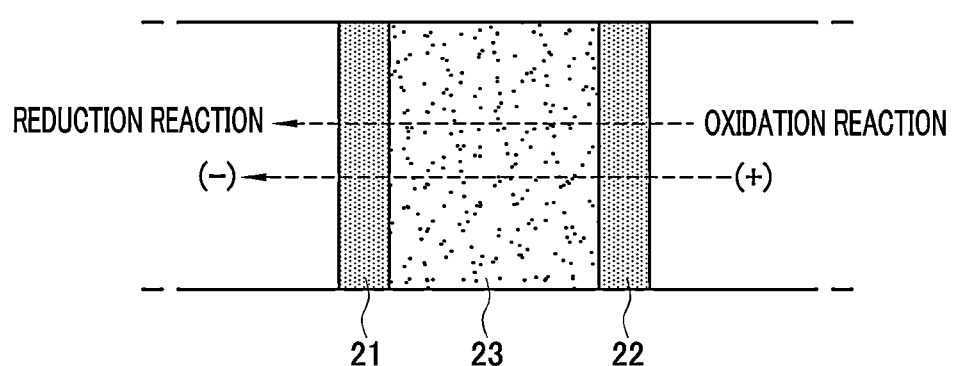

FIGS. 2B(i) and 2B(ii) illustrate an example in which the flow of the fluid in the pumping portion changes according to a reversible electrochemical reaction according to an example of the present invention.

In addition, the first electrode 21 and the second electrode 22 may not only change the flow of the fluid by utilizing an electrode material having a reversible electrode reaction, but also can return an electroactive material consumed by the positive reaction as the electrode reaction occurs in the reverse direction, to its original state. As described above, the first and second electrodes 21 and 22 can increase the life of the pump 10 by repeating consumption and regeneration.

Referring back to FIG. 1, the first and second diaphragms 11 and 12 configured on both sides of the pumping portion 13 are non-limiting examples and are formed of oil to form an oil gap, natural rubber formed of an elastic thin film, synthetic rubber, a metal plate, or the like. As the negative pressure and the positive pressure are alternately generated according to the driving of the pumping portion 13, at least a part thereof moves forward and backward to transmit the negative pressure and the positive pressure to the transport chamber 14 and the monitoring chamber 15.

For example, the first diaphragm 11 transmits the negative pressure and the positive pressure generated by the driving of the pumping portion 13, to the fluid to be transferred (Hereinafter, referred to as transport target fluid). More specifically, when the negative pressure is generated, at least a part of the first diaphragm 11 moves backward (that is, when a part of the first diaphragm 11 moves toward the monitoring chamber 15 based on FIG. 1 (illustrated by a long dotted line)), the transport target fluid is sucked into the transport chamber 14 and, on the contrary, when the positive pressure is generated, at least a part of the first diaphragm 11 moves forward (that is, when a part of the first diaphragm 11 moves toward the transport chamber 14 based on FIG. 1 (illustrated by a short dotted line)), the transport target fluid is discharged from the transport chamber 14.

In this case, suction and discharge of the transport target fluid are performed through the suction port 14a and the discharge port 14b formed on one surface of the transport chamber 14. The suction port 14a and the discharge port 14b are respectively coupled to a suction valve 17 and a discharge valve 18 which allow or block the flow of the transport target fluid, so that the transport target fluid can be sucked through the suction port 14a and can be discharged through the discharge port 14b. In other words, the suction valve 17 is closed when the first diaphragm 11 moves forward and is opened when the first diaphragm 11 moves backward, and the discharge valve 18 is opened when the first diaphragm 11 moves forward and is closed when the first diaphragm 11 moves backward. The suction valve 17 and the discharge valve 18 may be, for example, check valves, but are not limited thereto, and may be open/close devices that operate opposite to each other. In addition, in the above description, the suction valve 17 and the discharge valve 18 are described as being coupled to the pump 10, but the suction valve 17 and the discharge valve 18 may be implemented integrally with the pump 10.

Similar to the first diaphragm 11, the second diaphragm 12 repeatedly moves backward and forward by the driving of the pumping portion 13. Accordingly, by the movement of the second diaphragm 12, an air pressure in the monitoring chamber 15 changes. That is, when the negative pressure is generated, at least a part of the second diaphragm 12 moves backward (that is, when a part of the second diaphragm 12 moves toward the monitoring chamber 15 based on FIG. 1 (illustrated by a long dotted line)) and thereby the pressure in the monitoring chamber 15 is increased. Conversely, when the positive pressure is generated, at least a part of the second diaphragm 12 moves forward (that is, moves toward the transport chamber 14 based on FIG. 1 (illustrated by a short dotted line)), and thereby the air pressure in the monitoring chamber 15 is decreased.

The pressure measuring portion 16 is provided inside the monitoring chamber 15 to detect the pressure in the monitoring chamber 15 to convert the pressure into an electrical signal. For example, the pressure measuring portion 16 may be a pressure sensor that detects a pressure value as the second diaphragm 12 is deformed, based on a capacity change, a magnetic force change, a resistance displacement, and a voltage displacement of the monitoring chamber 15, or the like. Alternatively, the pressure measuring portion 16 may be a pressure sensor coupled to the second diaphragm 12 or integrally formed with the second diaphragm 12 to detect a pressure value based on the degree of deformation of the second diaphragm 12. However, the present invention is not limited thereto, and the pressure measuring portion 16 may measure the pressure inside the monitoring chamber 15 in various ways.

Figure 3A:
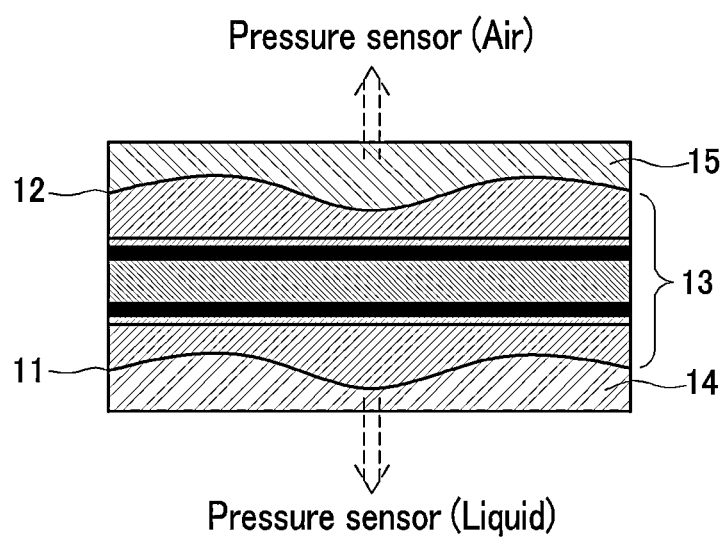
FIG. 3A is a view illustrating an experimental environment for experimenting a correlation between a pressure change appearing in a monitoring chamber according to driving of the pump and a pressure change measured in a transport target fluid.

FIG. 3A illustrates an experimental environment for experimenting a correlation between a pressure change appearing in the monitoring chamber according to the driving of the pump and a pressure change measured in the transport target fluid. A pressure sensor was disposed on one side of each of the transport chamber and the monitoring chamber for the experiment, and the pressure was measured in each of the transport chamber and the monitoring chamber after driving the pumping portion 13. At this time, the pump was used as an electroosmotic pump, and the pumping portion of FIGS. 2A(i) and 2A(ii) was used, and a voltage of 2.5 V was alternately applied to the electroosmotic pump, every 30 seconds.

Figure 3B:
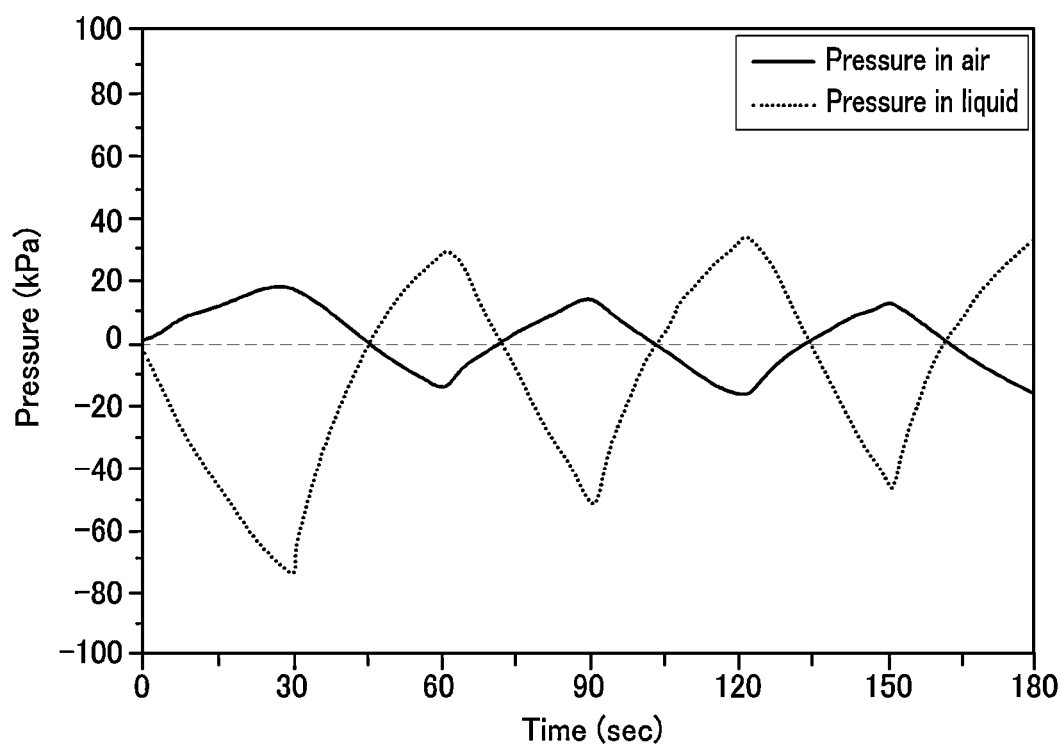
FIG. 3B is a graph for explaining an experimental result of FIG. 3A.

FIG. 3B illustrates an experimental result of FIG. 3A. A dotted line illustrates the pressure change measured in the pressure sensor provided on a transport chamber side, and a thick solid line illustrates the pressure change measured in the pressure sensor provided on a monitoring chamber side. In this case, since the positive pressure and the negative pressure are alternately generated in the pump, the pressure change is represented by a wave (that is, a swing wave) pattern having an amplitude and a period.

As illustrated in FIG. 3B, the pressure changes measured respectively in the transport chamber and the monitoring chamber appear in forms of swing waves with opposite polarities in the same period. This is because at least a part of the first and second diaphragms 11 and 12 moves forward or backward, so that the capacities of the transport chamber and the monitoring chamber increase or decrease oppositely. However, it can be seen that an intermediate value of the swing wave corresponding to the transport chamber (that is, an average of the pressure values for a predetermined time) and an intermediate value of the swing wave corresponding to the monitoring chamber are the same or similar. That is, it can be seen that the pressure change of the transport target fluid can be indirectly monitored using the average value of the pressure values measured in the monitoring chamber.

Therefore, the pump 10 according to an example of the present invention can monitor the pressure change of the transport target fluid by providing a single pressure sensor in the monitoring chamber 15 formed on one side of the second diaphragm 12. That is, the pump 10 according to an example of the present invention does not include a pressure sensor directly in the flow path, so that the pressure of the transport target fluid can be monitored without contaminating the transport target fluid. This not only makes it possible to monitor the state of the pump 10, but also facilitate maintenance of the pressure sensor.

Furthermore, in the pump 10 according to an example of the present invention, the pressure value measured in the monitoring chamber 15 is provided to the system using the pump 10 so that the system can effectively detect abnormality of the pump 10. Hereinafter, a fluid transport system (for example, a fluid injection system or a fluid extraction system) using the pump 10 will be described as an example.

Figure 4:
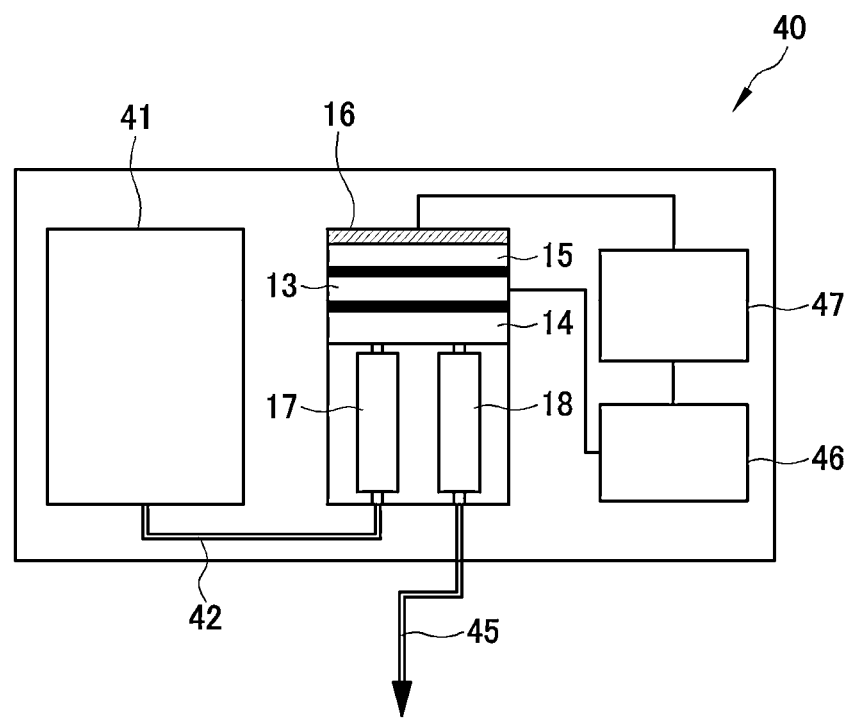
FIG. 4 is a block diagram illustrating a configuration of a fluid transport system using the pump of FIG. 1 according to an example of the present invention.

FIG. 4 is a block diagram illustrating a configuration of a fluid transport system 40 using the pump 10 of FIG. 1.

Referring to FIG. 4, the fluid transport system 40 includes the pump 10 of FIG. 1; a reservoir 41 in which the transport target fluid is stored; a suction path 42 which is a fluid transport path of the transport target fluid and through which the transport target fluid discharged from the reservoir 41 is sucked into the pump 10; a discharge path 45 which is a fluid transport path of the transport target fluid discharged from the pump 10; and a control circuit 47 which detects the abnormality of the pump 10 by monitoring a pressure value measured by the pressure measuring portion 16. In addition, the fluid transport system 40 may further include a power supply portion 46 for supplying the electric power to the pump 10 and the control circuit 47.

The pump 10 includes the first and second diaphragms 11 and 12 which are provided on both sides of the pumping portion 13 alternately generating the positive pressure and the negative pressure, and of which the shapes are changed according to the positive pressure and the negative pressure; the transport chamber 14 which sucks and discharges the transport target fluid according to the shape change of the first diaphragm 11; the monitoring chamber 15 of which the pressure changes according to the shape change of the second diaphragm 12; and the pressure measuring portion 16 measuring the pressure of the monitoring chamber 15. Since the configuration of the pump 10 is described above with reference to FIGS. 1 to 3B, detailed description thereof will be omitted.

Both ends of the suction path 42 are respectively coupled to the discharge port of the reservoir 41 and the suction valve 17 (or the suction port 14a of the transport chamber 14), to move the transport target fluid stored in the reservoir 41 to the transport chamber 14 of the pump 10. One end of the discharge path 45 is coupled to the discharge valve 18 (or the discharge port 14b of the transport chamber 14), and the other end is inserted into a target body to transport (that is, inject) the transport target fluid to the target body. For example, the discharge path 45 may include a catheter, a cannula, an infusion needle, or the like to be injected into the target body.

The reservoir 41 is a storage container for storing the transport target fluid, which is formed of a material that can block external gas and ions, and of which one side is coupled to the suction path 42 to discharge the transport target fluid in synchronization with the driving of the pump 10. That is, when the negative pressure is generated by the driving of the pump 10, the suction valve 17 is opened to move the transport target fluid stored in the reservoir 41 to the suction valve 17 through the suction path 42. On the contrary, when the positive pressure is generated, the suction valve 17 is closed to stop the movement of the transport target fluid. In this case, since the discharge valve 18 is opened, the transport target fluid may be injected into the target body through the discharge path 45 coupled to the discharge valve 18.

Figure 5:
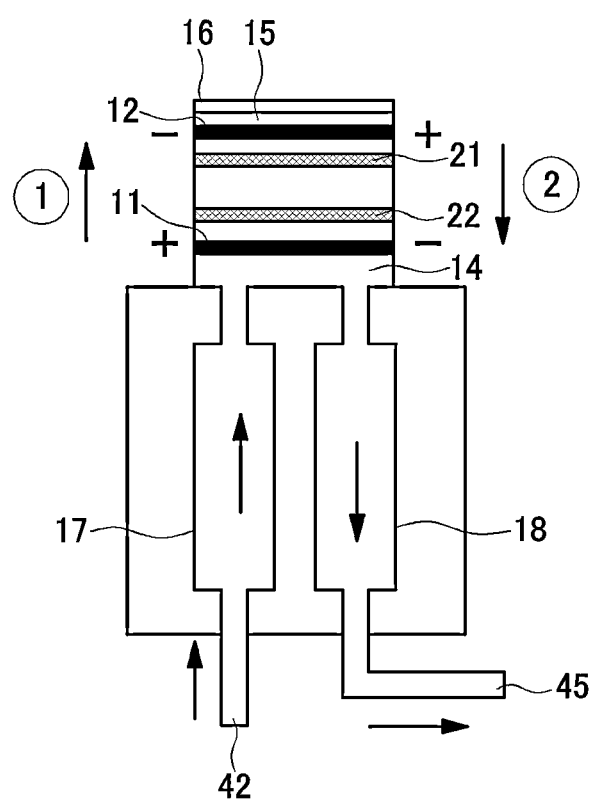
FIG. 5 is a view for explaining a principle that the transport target fluid moves in the fluid transport system according to an example of the present invention.

FIG. 5 is a view for explaining a principle of the movement of the transport target fluid in the fluid transport system 40 according to an example of the present invention. In FIG. 5, it is assumed that the pumping portion 13 of FIGS. 2A(i) and 2A(ii) is used.

Referring to FIG. 5, when a negative voltage is applied to the first electrode 21 and a positive voltage is applied to the second electrode 22 of the pumping portion 13, the negative pressure is generated. By the negative pressure, the transport target fluid is moved in a direction ①. At this time, the discharge valve 18 is closed, so that the negative pressure is not transmitted to the discharge path (45).

On the contrary, when a positive voltage is applied to the first electrode 21 and a negative voltage is applied to the second electrode 22 of the pumping portion 13, the positive pressure is generated in the opposite direction by a reversible electrochemical reaction. Therefore, the transport target fluid sucked into the transport chamber 14 is moved in a direction ② through the discharge valve 18. At this time, the suction valve 17 is blocked, so that the positive pressure is not transmitted to the reservoir 41. Therefore, the transport target fluid moved in the direction ② is moved to the discharge path 45 to be injected into the target body.

On the other hand, the suction path 42 and the discharge path 45 may be formed of circular tubes (or pipes) of various materials capable of moving the transport target fluid but are not limited thereto. In addition, coupling means may be provided at both ends of (that is, coupling portions to the reservoir 41 and the suction valve 17, respectively) the suction path 42 and the other end (that is, a coupling portion to the discharge valve 18) of the discharge path 45, and each O-ring (not illustrated) may be coupled thereto to remove a gap.

The power supply portion 46 is electrically connected to the control circuit 47 and the pump 10 to supply the electric power to a motor (not illustrated) or an electrode (not illustrated) of the pumping portion 13 by control of the control circuit 47.

For example, in a case in which the pump 10 is an electroosmotic pump, the power supply portion 46 may be implemented by including a DC supply device (not illustrated) for supplying a DC voltage to each of the first electrode 21 and the second electrode 22 illustrated in FIGS. 2B(i) and 2B(ii), to alternately supplying the polarities of the voltage, and a switching device (not illustrated) for alternately switching polarities of the DC voltage supplied to each of the first and second electrodes 21 and 22, at every predetermined time. Therefore, the voltage applied to each of the first electrode 21 and the second electrode 22 may be changed to the opposite polarity at every predetermined time. However, the present invention is not limited to the above-described example, and the power supply portion 46 may be implemented as an AC supply device (not illustrated) for supplying a stirring current at a constant cycle.

The control circuit 47 includes one or more circuit elements for monitoring the abnormality of the pump 10 based on the pressure value provided from the pressure measuring portion 16. For example, the control circuit 47 may be implemented as a field-programmable gate array (FPGA) or an application specific integrated circuit (ASIC). On the other hand, in an implementation example, the control circuit 47 and the power supply portion 46 may be mounted on a printed circuit board (PCB).

Figure 6:
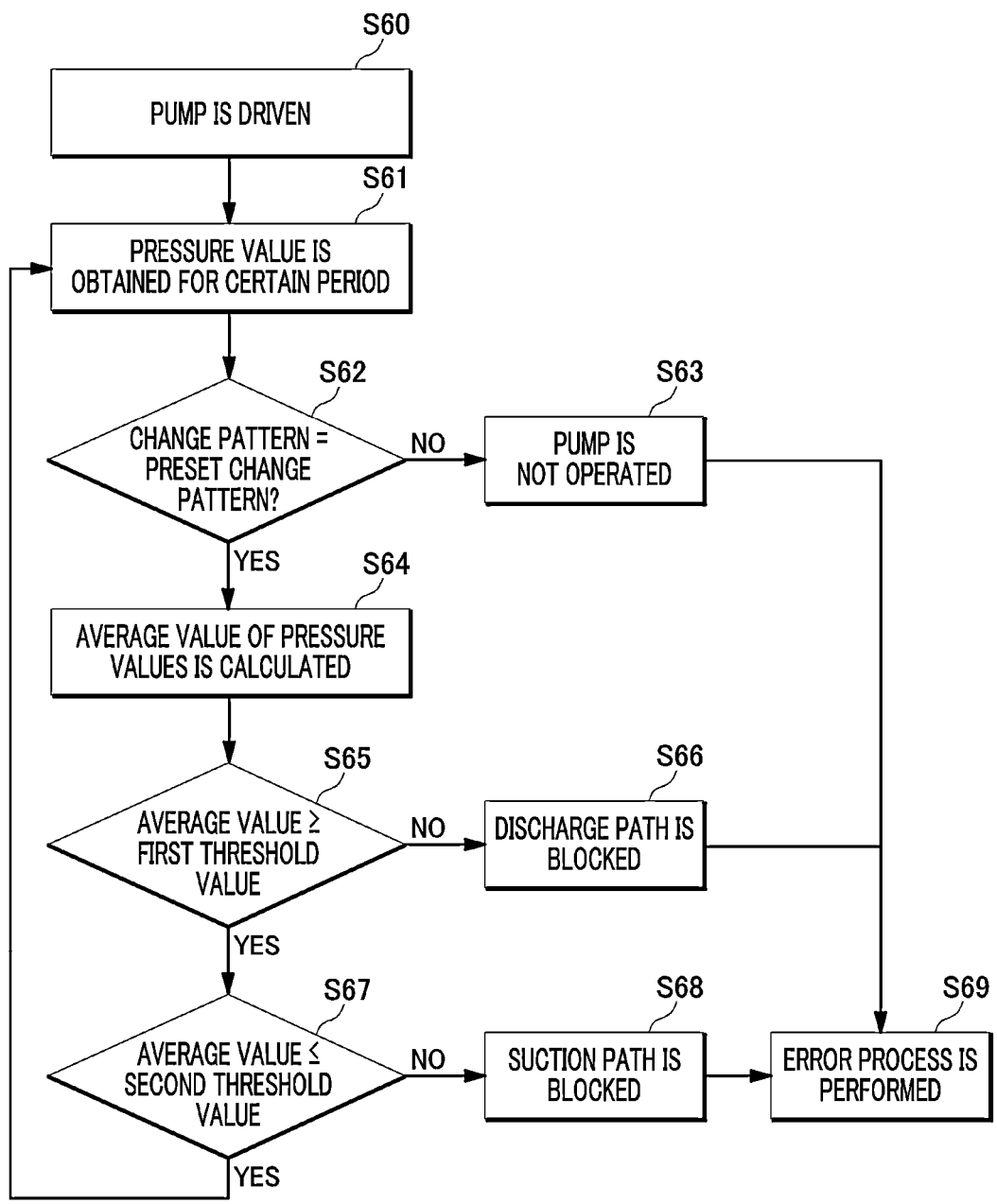
FIG. 6 is a flowchart illustrating a method of detecting abnormality of a pump by a control circuit according to an example of the present invention.

FIG. 6 is a flowchart illustrating a method of detecting the abnormality of the pump 10 by the control circuit 47 according to an example of the present invention.

First, the control circuit 47 drives the pump 10 (S60). The control circuit 47 controls the power supply portion 46 to alternately supply voltages having different polarities to the pumping portion 13 of the pump 10. Accordingly, the pumping portion 13 alternately generates the positive pressure and the negative pressure, thereby changing the shapes of the first and second diaphragms 11 and 12. In other words, at least a part of the first and second diaphragms 11 and 12 is moved forward or backward in the same direction as the positive pressure and the negative pressure are alternately generated.

As the shapes of the first and second diaphragms 11 and 12 are repeatedly deformed (that is, moving forward or backward), the transport target fluid is sucked and discharged in the transport chamber formed on one side of the first diaphragm 11. In addition, the control circuit 47 receives a pressure value from the pressure measuring portion 16 provided in the second diaphragm 12 (S61).

The control circuit 47 detects the abnormality of the pump 10 based on the pressure value measured by the pressure measuring portion 16. For example, the control circuit 47 may detect non-operation of the pumping portion of the pump and the blockage of the fluid path based on a change pattern of the pressure value measured for a predetermined time and an average value of the pressure values measured for the predetermined time. Here, the predetermined time may correspond to an alternating cycle of the power supply applied alternately to the pump 10 but is not limited thereto.

More specifically, the control circuit 47 detects whether or not the change pattern of the pressure value measured for a predetermined period corresponds to a preset pattern (S62). In this case, as described above with reference to FIG. 3B, the preset pattern may be a wave (that is, a swing wave) having an amplitude and a period equal to or greater than a preset intensity.

If the change pattern of the pressure value does not correspond to the preset pattern, the control circuit 47 determines that the pumping portion 13 is not operated (S63), and then performs an error process (S69). Here, the fact that the change pattern of the pressure value does not correspond to the preset pattern (that is, the swing wave) means that the pumping portion 13 is not operated so that the positive pressure and the negative pressure are not alternately generated. That is, in a case in which the change pattern of the pressure value appears in a form of a straight line or a curve without period and/or amplitude, the control circuit 47 may determine that the pumping portion 13 is not operated. In addition, the error process is a program executed by the control circuit 47 when an error occurs in the fluid transport system 40 and may include one or more instructions for performing at least one of user notification and system state analysis. For example, the program may notify a notification device (not illustrated) such as a speaker, a display, or an LED included in the fluid transport system 40 of the fact that the pump 10 is not operated or may notify a terminal of a user of the fact through a communication portion (not illustrated). State information of the power supply portion 46 may be read to analyze the power supply state to the pump 10.

However, in step S62, in a case in which the change pattern of the pressure value corresponds to the preset pattern, the control circuit 48 determines that the pumping portion 13 of the pump 10 is normally operated, and then calculates the average value of the pressure values measured for a predetermined time (S64). For example, the control circuit 47 may calculate the average value of the pressure values measured for a predetermined time, or calculate an intermediate value between a highest value and a lowest value of the pressure values measured for a predetermined time.

Thereafter, the control circuit 47 detects whether or not the flow path is blocked by comparing the average value with a threshold range. In a case in which blockage occurs on the discharge path side of the pump 10, the transport target fluid is not normally sucked into the pump 10 or is not normally discharged. Therefore, the pressure of the transport chamber 14 in the pump 10 is increased, and thereby the first diaphragm 11 moves backward (that is, deformed in the direction toward the monitoring chamber 15 based on FIG. 1) by the pressure of the transport chamber 14 regardless of the operation of the pumping portion 13. This causes the gas or the fluid in the pumping portion 13 to move backward, thereby moving the second diaphragm 12 backward. As a result, the pressure in the monitoring chamber 15 becomes abnormally high.

On the contrary, in a case in which blockage occurs on the suction path side, the transport target fluid cannot be normally sucked into the pump 10, so that the pressure in the transport chamber 14 is decreased. This causes the first diaphragm 11 to move forward (that is, deformed in the direction toward the liquid chamber 14 based on FIG. 1), and the gas or the fluid in the pumping portion 13 to continuously move forward. Accordingly, the second diaphragm 12 moves forward regardless of the operation of the pumping portion 13, and the pressure in the monitoring chamber 15 is abnormally decreased. The control circuit 47 detects whether or not the flow path is blocked by using whether or not the pressure change in the monitoring chamber 15 is outside a critical range.

Specifically, the control circuit 47 determines (S66) that the blockage occurs in the discharge path of the transport target fluid based on the pump 10 when the average value of the pressure values is equal to or greater than the critical range for a predetermined time (S65), and the error process is performed (S69). In other words, the control circuit 47 determines that the blockage of the flow path occurs in the discharge path 45 and/or the discharge valve 18 and performs the error process corresponding thereto. In this case, as described above, the error process may perform at least one of the user notification and the system state analysis, and thus a detailed description thereof will be omitted.

Alternatively, if the average value of the pressure values is less than or equal to the threshold range for a predetermined time (S67), the control circuit 47 determines that blockage occurs in the suction path of the transport target fluid based on the pump 10 (S68), and performs the error process (S69). In other words, the control circuit 47 determines that the blockage of the flow path occurs in the suction path 42 and/or the suction valve 17 and performs the error process corresponding thereto.

On the other hand, if the change pattern of the pressure value for a predetermined time corresponds to the preset pattern, and the average value of the pressure values is within the threshold range, the control circuit 47 may repeat the process of S61 or below.

In addition, the preset pattern and the threshold range are values experimentally determined based on the case in which the abnormality occurs in the fluid transport system and may be preset values in a manufacturing step.

On the other hand, in the above description, the fluid transport system injects the fluid into the target body, but as described above, the fluid transport system may extract the fluid from the target body. In this case, the discharge path described above is, for example, a microfiltration (MF) probe, an ultrafiltration (UF) probe, or the like, and functions as the suction path. The suction path functions as the discharge path and can discharge the transport target fluid extracted from the target body to the outside or move the transport target fluid to the reservoir.

FIGS. 7 to 10 are examples of experimental results of detecting the non-operation of the pumping portion and blockage of the flow path using the fluid transport system according to an example of the present invention.

Figure 7:
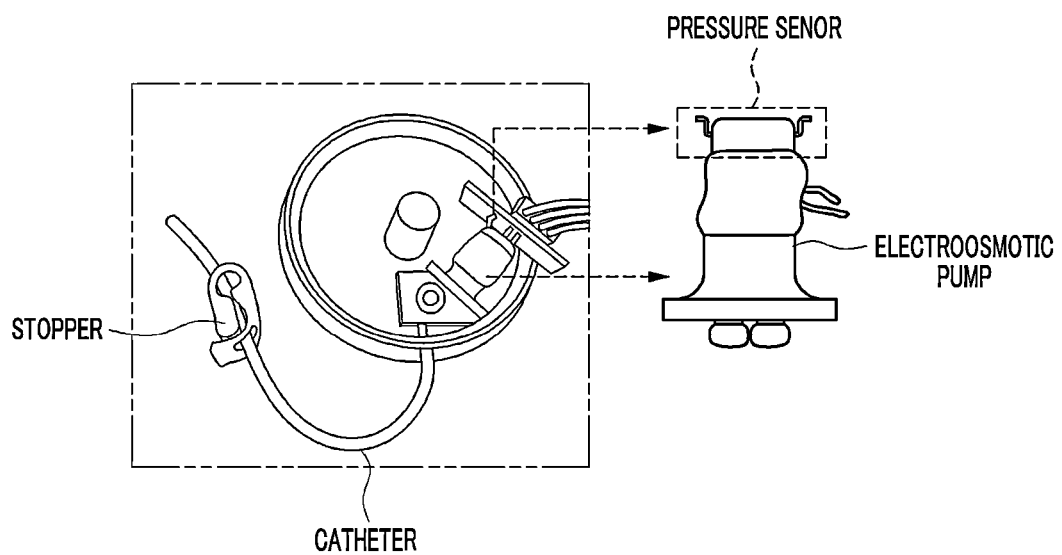
FIG. 7 is a view illustrating a fluid transport system used in the experiment.

FIG. 7 illustrates the fluid transport system used in the experiment. In this case, the pump was the electroosmotic pump, the pumping portion of FIGS. 2A(i) and 2A(ii) was used, and the pressure sensor was attached to the outside of an upper end of the electroosmotic pump to measure the pressure value. In this case, a voltage of 2.5 V is alternately applied to the electroosmotic pump at 30 second intervals, and the electroosmotic pump was configured to suck/discharge the liquid of the reservoir at 30 second intervals. In addition, a stopper was located in the flow path to simulate the blockage of the flow path.

Figure 8:
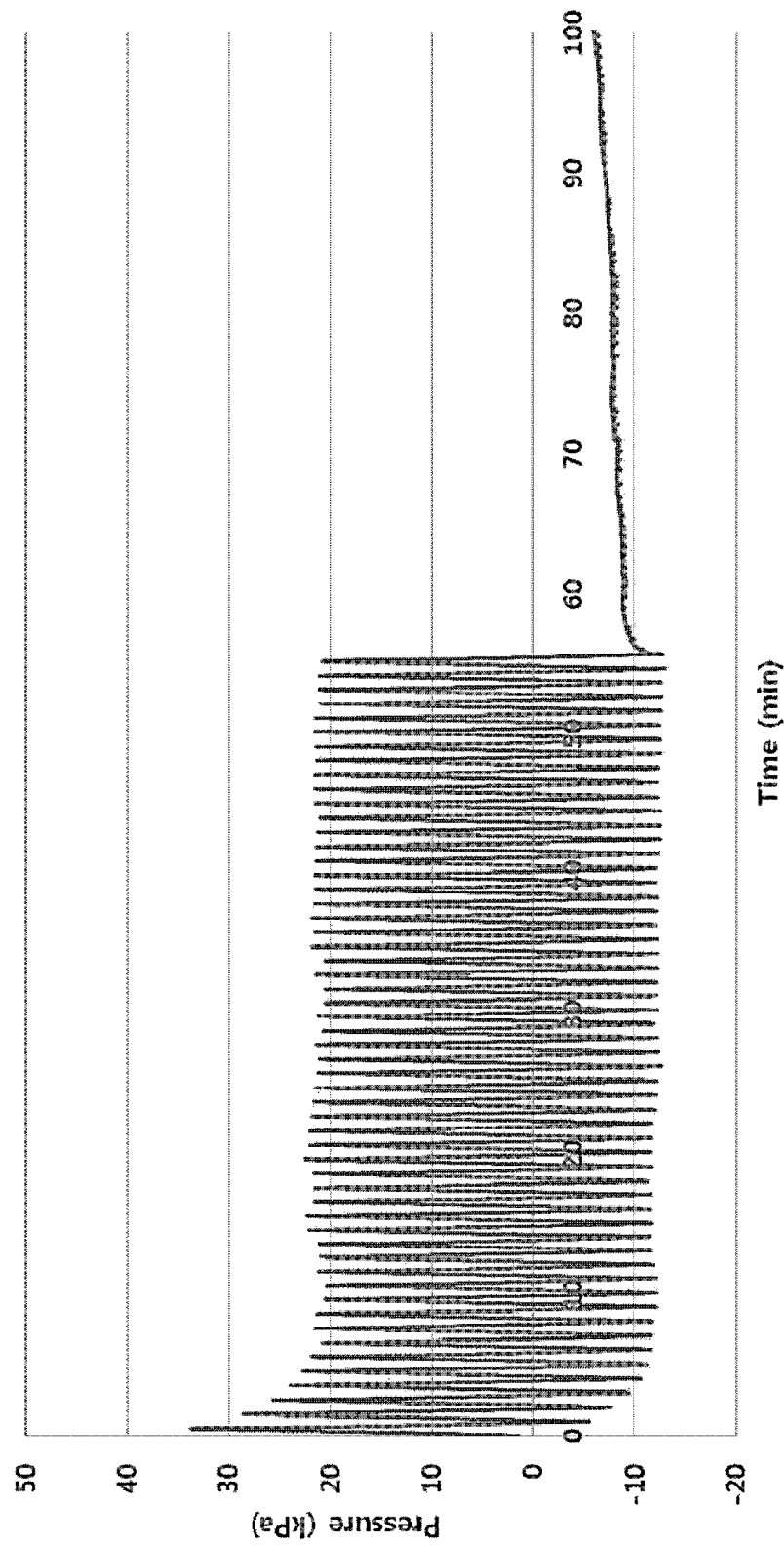
FIG. 8 is a graph for explaining an experimental result of detecting non-operation of the pumping portion using the fluid transport system of FIG. 7.

FIG. 8 illustrates a pressure change in a case in which the operation of the electroosmotic pump is artificially stopped, as an experimental result of detecting the non-operation of the pumping portion using the fluid transport system of FIG. 7. As illustrated in FIG. 8, it can be seen that when the electroosmotic pump normally operates (that is, 0 to 55 seconds), a pressure change pattern of a wave form appears by driving the electroosmotic pump, but after the electroosmotic pump is artificially stopped, a linear pressure change appears.

Figure 9:
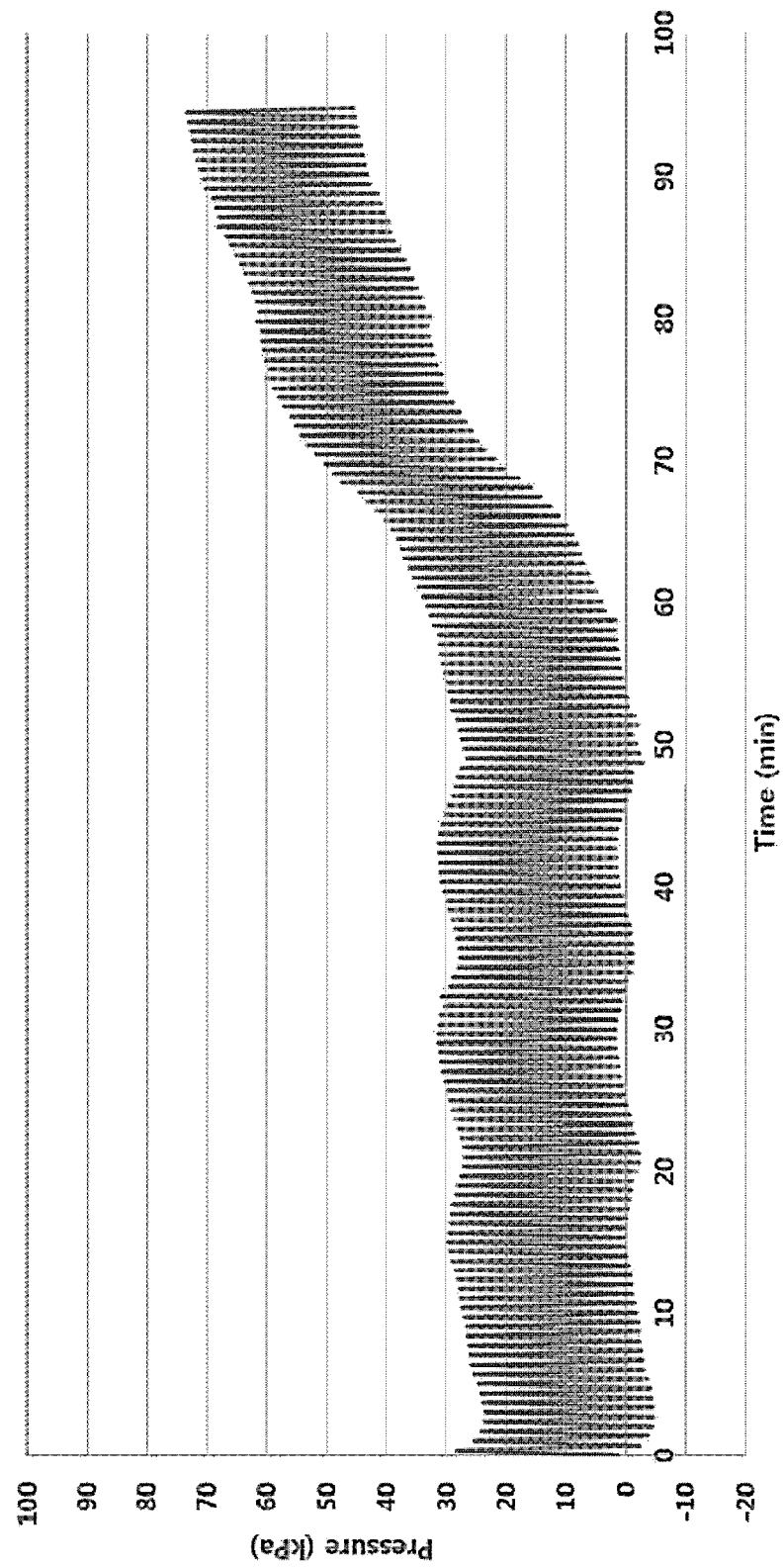
FIGS. 9 and 10 are graphs for explaining experimental results of detecting blockage of the flow path using the fluid transport system of FIG. 7.
Figure 10:
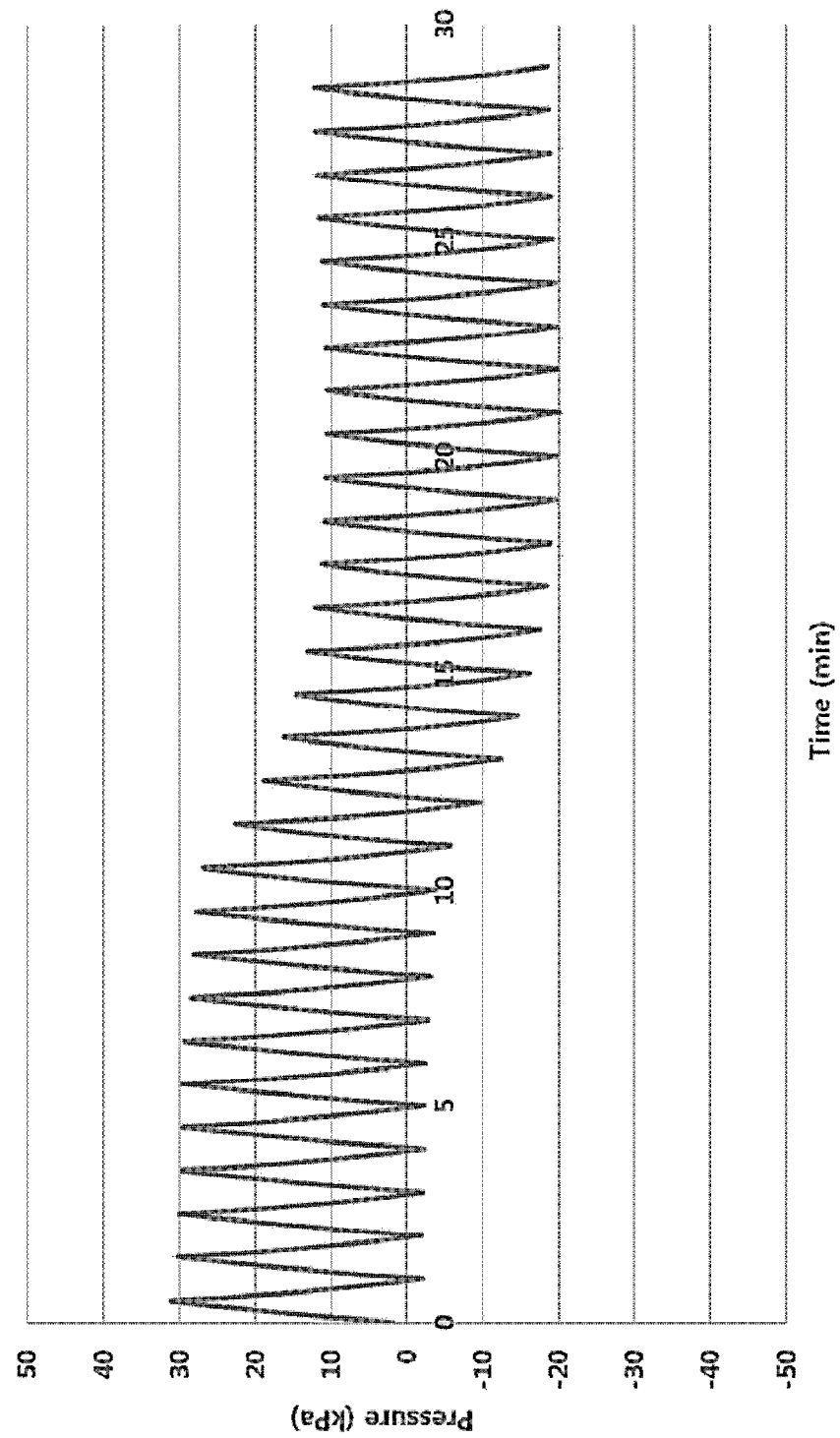

FIGS. 9 and 10 illustrate experimental results of detecting the blockage of the flow path using the fluid transport system of FIG. 7. In FIG. 9, the stopper was located in the catheter to artificially block the catheter after about 60 seconds. Accordingly, it can be seen that the pressure value measured after about 60 seconds gradually increases. In FIG. 10, the stopper was moved to the suction path side of the electroosmotic pump to artificially block the suction path after about 10 seconds. Accordingly, it can be seen that the pressure value measured after about 10 seconds was decreased.

As described above, the fluid transport system using the pump according to an example of the present invention moves the transport target fluid on one side of the first diaphragm 11, and forms an air layer of a closed system on one side of the second diaphragm 12 to monitor the pressure in the air layer. Therefore, it is possible to easily detect the non-operation of the pump and the blockage of the flow path of the system.

A method of operating the fluid transport system according to an example of the present invention described above may be implemented in a form of a recording medium including instructions executable by a computer, such as a program module executed by a computer. The computer readable medium may be any available media that can be accessed by the computer and includes all volatile and nonvolatile media, and removable and non-removable media. In addition, the computer readable medium may include a computer storage medium. The computer storage medium includes all volatile and nonvolatile media, and removable and non-removable media implemented in any method or technology for storing information such as computer readable instructions, data structures, program modules, or other data.

Although the system and method of the present invention are described in connection with specific examples, some or all of their configuration elements or operations may be implemented using a computer system having a general hardware architecture.

It will be appreciated that the description described above of the present invention is intended for illustration, and it will be understood by those skilled in the art that the present invention may be easily modified in other specific forms without changing the technical spirit or essential features of the present invention. Therefore, it should be understood that the examples described above are exemplary in all respects and not restrictive. For example, each configuration element described as a single type may be implemented in a distributed manner, and similarly, the configuration elements described as distributed may be implemented in a combined form.

The scope of the present invention is illustrated by the following claims rather than the detailed description, and all changes or modifications derived from the meaning and scope of the claims and their equivalents should be construed as being included in the scope of the present invention.

What is claimed is:

1. An electroosmotic pump comprising:
a pumping portion alternately generating a positive pressure and a negative pressure by a reversible electrochemical reaction;
a first diaphragm which is provided on one side of the pumping portion and of which a shape is changed as the positive pressure and the negative pressure are alternately generated;
a transport chamber which is provided on one side of the first diaphragm, and sucks and discharges a transport target fluid corresponding to the deformation of the first diaphragm;
a second diaphragm which is provided on the other side of the pumping portion and of which a shape is changed as the positive pressure and the negative pressure are alternately generated; and
a monitoring chamber which is provided on one side of the second diaphragm and of which a pressure changes corresponding to the deformation of the second diaphragm.

2. The electroosmotic pump according to claim 1, further comprising:
a pressure measuring portion measuring a pressure change of the monitoring chamber.

3. The electroosmotic pump according to claim 1,
wherein one surface of the transport chamber is formed with a suction port and a discharge port through which the suction and discharge of the transport target fluid are performed, and
wherein a suction valve and a discharge valve for allowing or blocking the flow of the transport target fluid are coupled to the suction port and the discharge port, respectively.

4. The electroosmotic pump according to claim 3,
wherein the suction valve is closed when a positive pressure is generated and is opened when a negative pressure is generated, and
wherein the discharge valve is opened when the positive pressure is generated and is closed when the negative pressure is generated.

5. The electroosmotic pump according to claim 3,
wherein the suction valve and the discharge valve are check valves.

6. The electroosmotic pump according to claim 2,
wherein the pressure measuring portion is a pressure sensor that is provided in the monitoring chamber and detects a pressure of the monitoring chamber based on at least one of a capacity change, a magnetic force change, a resistance displacement, and a voltage displacement of the monitoring chamber as the second diaphragm is deformed.

7. The electroosmotic pump according to claim 2,
wherein the pressure measuring portion is a pressure sensor that detects a pressure of the monitoring chamber based on a deformation degree of the second diaphragm.

8. The electroosmotic pump according to claim 1,
wherein the pumping portion includes a first electrode and a second electrode provided on both sides of a membrane installed in, a fluid path portion through which a first fluid moves, and alternately generates a positive pressure and a negative pressure as polarities of voltages are alternately supplied to the first electrode and the second electrode, and
wherein the first electrode and second electrode are formed of a porous material to allow movement of the first fluid.

9. The electroosmotic pump according to claim 8,
wherein the positive pressure and negative pressure are generated by a reversible electrochemical reaction in first electrode and second electrode, and
wherein the reversible electrochemical reaction of first electrode and second electrode is caused by movement of cations in a direction of charge balancing.

10. The electroosmotic pump according to claim 9,
wherein each of the first electrode and the second electrode is repeatedly consumed and regenerated by the reversible electrochemical reaction.

11. The electroosmotic pump according to claim 8,
wherein the first electrode and the second electrode include a conductive polymer in which an anionic polymer is mixed.

12. The electroosmotic pump according to claim 8,
wherein the first electrode and the second electrode include carbon nanostructures.

13. The electroosmotic pump according to claim 7,
wherein the first electrode and the second electrode include metal oxides selected from the group consisting of oxide (MnOx), cobalt oxide (CoOx), nickel oxide (NiOx), ruthenium oxide (RuOx), and composites thereof.

14. A fluid transport system using a pump provided with a plurality of diaphragms, the fluid transport system comprising:
a pump including a first diaphragm and a second diaphragm which are provided on both sides of a pumping portion alternately generating a positive pressure and a negative pressure by a reversible electrochemical reaction, and of which shapes are changed according to the positive pressure and the negative pressure, a transport chamber which sucks and discharges a transport target fluid according to the shape change of the first diaphragm, and a monitoring chamber of which a pressure changes according to the shape change of the second diaphragm;
a reservoir in which the transport target fluid is stored;
a suction path that is a fluid transport path through which the transport target fluid discharged from the reservoir is sucked to the pump;
a discharge path that is a fluid transport path of the transport target fluid discharged from the pump; and
a control circuit detecting abnormality of the pump by monitoring a pressure value measured by the pressure measuring portion.

15. The fluid transport system according to claim 14, wherein the pump includes a pressure measuring portion measuring a pressure of the monitoring chamber.

16. The fluid transport system according to claim 14,
wherein the control circuit detects non-operation of the pumping portion of the pump and blockage of the fluid path based on a change pattern of the pressure value measured for a predetermined time and an average value of the pressure values measured for the predetermined time.

17. The fluid transport system according to claim 16,
wherein the control circuit determines that the pumping portion of the pump normally operates when the change pattern of the pressure value corresponds to a preset pattern, and determines that the pumping portion of the pump is not operated when the change pattern of the pressure value does not correspond to the preset pattern, and
wherein the preset pattern is a wave form having a preset amplitude and period.

18. The fluid transport system according to claim 16,
wherein the control circuit determines that the discharge path is blocked when the average value of the pressure values is equal to or greater than a threshold range.

19. The fluid transport system according to claim 16,
wherein the control circuit determines that the suction path is blocked when the average value of the pressure values during the predetermined time is equal to or less than a threshold range.

20. The fluid transport system according to claim 14,
wherein a suction port and a discharge port are formed on one surface of the pump to suck and discharge the transport target fluid, and
wherein a suction valve and a discharge valve for allowing or blocking the flow of the transport target fluid are coupled to the suction port and the discharge port, respectively.

21. The fluid transport system according to claim 14,
wherein one end of the suction path is coupled to the discharge port provided on one side of the reservoir and the other end is coupled to the suction valve, and
wherein one end of the discharge path is coupled to the discharge valve and the other end is injected to a target body.

22. The fluid transport system according to claim 20,
wherein the discharge path is at least one of a catheter, a cannula, and an infusion needle.

23. The fluid transport system according to claim 20,
wherein at least a part of each of the first diaphragm and the second diaphragm is moved toward the monitoring chamber as the negative pressure is generated in the pump, and is moved toward the transport chamber as the positive pressure is generated in the pump.

24. The fluid transport system according to claim 14,
wherein the pumping portion of the pump includes a first electrode and a second electrode provided on both sides of a membrane, a fluid path portion, and alternately generates a positive pressure and a negative pressure as polarities of voltages are alternately supplied to the first electrode and the second electrode, and
wherein the first electrode and the second electrode are formed of a porous material to allow movement of the fluid.

25. The fluid transport system according to claim 24,
wherein the positive pressure and the negative pressure are generated by reversible electrochemical reactions in first electrode and second electrode, and
wherein the reversible electrochemical reactions of first electrode and second electrode are caused by movement of cations in a direction of charge balancing.

* * * * *